US00PP24609P3

(12) United States Plant Patent
Sills et al.

(10) Patent No.: US PP24,609 P3
(45) Date of Patent: Jul. 8, 2014

(54) BLACKBERRY PLANT NAMED 'DRISBLACKFOUR'

(50) Latin Name: ***Rubus* L. subgenus *Rubus***
Varietal Denomination: DrisBlackFour

(75) Inventors: Gavin R. Sills, Watsonville, CA (US); Jorge Rodriguez Alcazar, Texcoco (MX); Jose Maurilio Rodriguez Mesa, Michoacan (MX); Andrea M. Pabon, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 182 days.

(21) Appl. No.: 13/507,940

(22) Filed: Aug. 8, 2012

(65) Prior Publication Data

US 2014/0047593 P1 Feb. 13, 2014

(51) Int. Cl.
*A01H 5/00* (2006.01)

(52) U.S. Cl.
USPC ..... Plt./203

(58) Field of Classification Search
USPC ..... Plt./203
See application file for complete search history.

(56) References Cited

U.S. PATENT DOCUMENTS

PP23,497 P3 * 3/2013 Clark et al. ..... Plt./203
PP24,249 P3 * 2/2014 Clark ..... Plt./203

* cited by examiner

*Primary Examiner* — Wendy C Haas
(74) *Attorney, Agent, or Firm* — Jondle Plant Sciences division of Swanson & Bratschun, L.L.C.

(57) ABSTRACT

This invention relates to a new and distinct variety of Blackberry plant named 'DrisBlackFour', particularly characterized by improved storage life, late flowering season, and excellent fruit flavor and appearance, is disclosed.

2 Drawing Sheets

Genus and species: *Rubus* L. subgenus *Rubus*.
Variety denomination: 'DrisBlackFour'.

BACKGROUND OF THE NEW PLANT

The present invention relates to a new and distinct blackberry cultivar designated 'DrisBlackFour' and botanically known as *Rubus* L. subgenus *Rubus*. This new blackberry variety was identified in Ventura County, Calif. in April 2005 and originated from a cross between the female parent blackberry plant 'Sleeping Beauty' (U.S. Plant Pat. No. 13,758) and the male parent blackberry plant 'BH917-6' (unpatented). The original seedling of the new cultivar was first asexually propagated at a nursery in Santa Cruz County, Calif. in 2005. 'DrisBlackFour' was subsequently asexually propagated and underwent further testing at a nursery in Los Reyes, Mexico from 2007 to 2010. The present invention has been found to be stable and reproduce true to type through successive asexual propagations.

Plant Breeder's Rights for this variety have not been applied for. 'DrisBlackFour' has not been made publicly available or sold more than one year prior to the filing date of this application.

SUMMARY OF THE INVENTION

The following are the most outstanding and distinguishing characteristics of this new cultivar when grown under normal horticultural practices in Los Reyes, Mexico.

1. Improved storage life;
2. Late flowering season; and
3. Excellent fruit flavor and appearance.

DESCRIPTION OF THE PHOTOGRAPHS

This new Blackberry plant is illustrated by the accompanying photographs which show the plant's canes, fruit, and leaves. The colors shown are as true as can be reasonably obtained by conventional photographic procedures. The photographs are of plants that are 2 years old.

Figure 1:
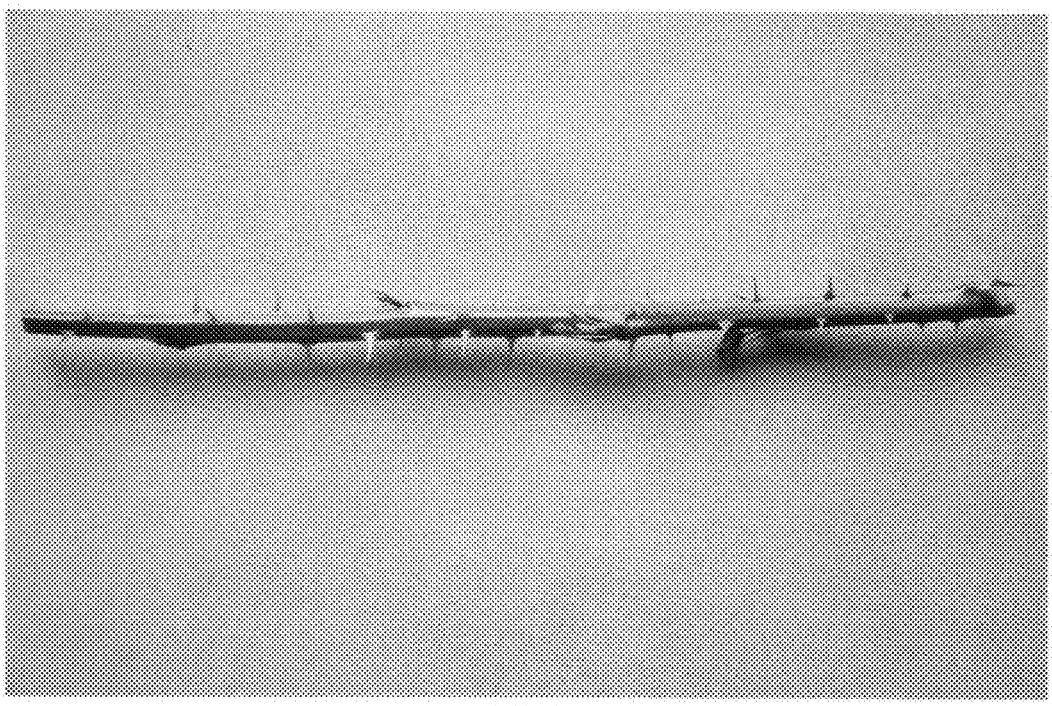
Figure 2:
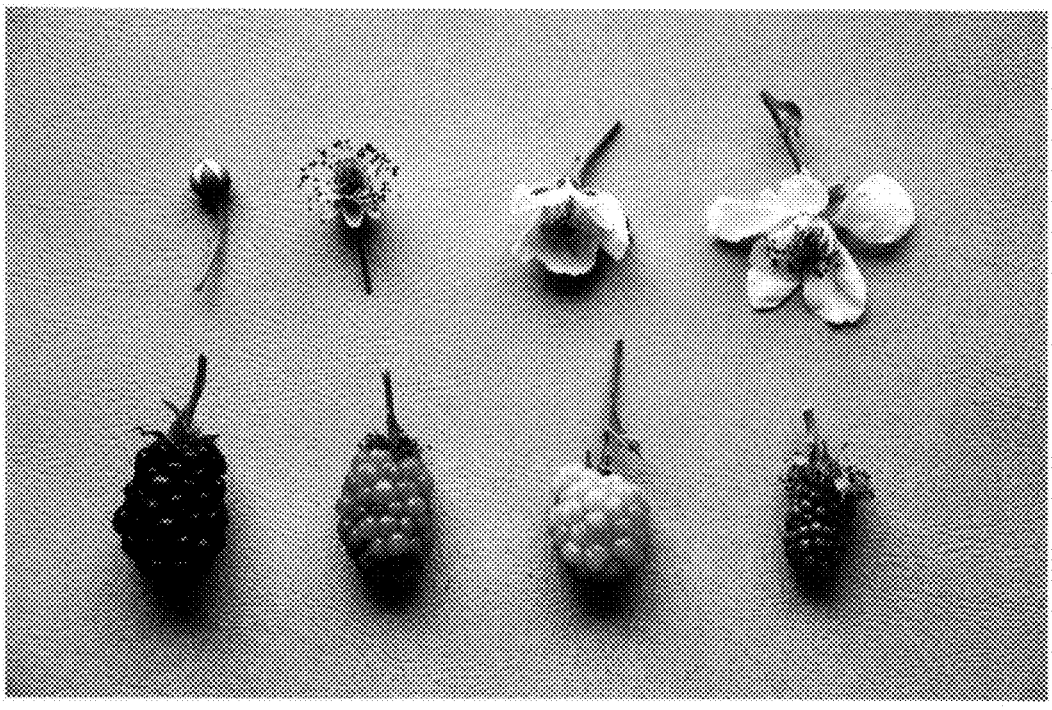
Figure 3:
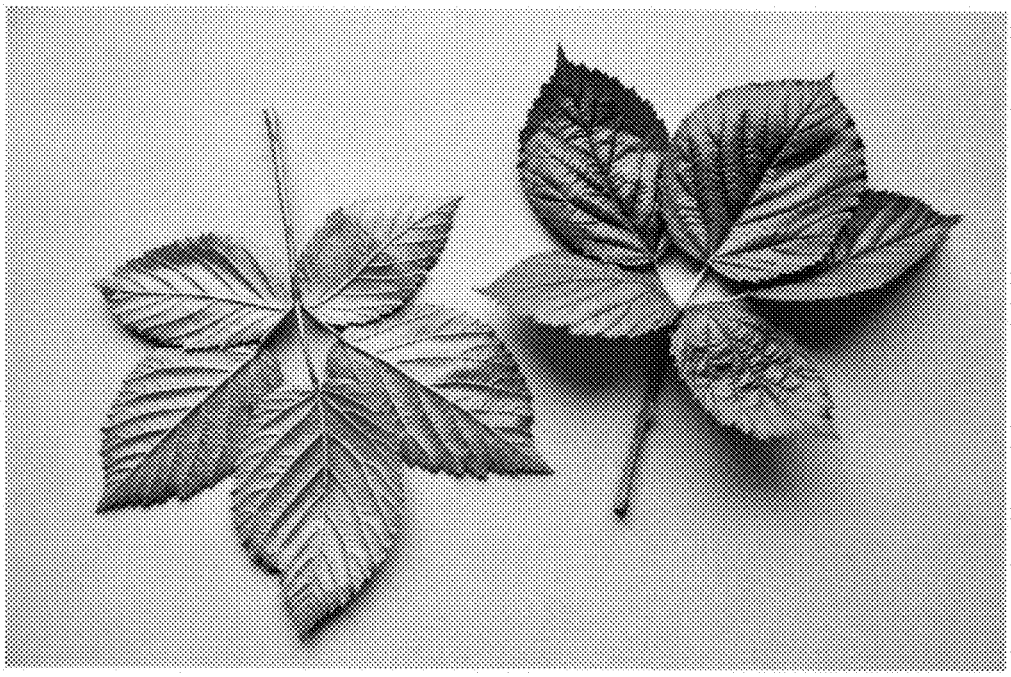

FIG. 1 shows a section of a young cane with spines.
FIG. 2 shows the flowers and the fruit at various stages.
FIG. 3 shows the upper and lower surfaces of the leaves.

DESCRIPTION OF THE NEW VARIETY

The following descriptions of 'DrisBlackFour' are based on observations made in Los Reyes, Mexico on 2-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackFour' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* $2^{nd}$ edition, by James G. Harris and Melinda Woolf Harris, unless where otherwise defined.

DETAILED BOTANICAL DESCRIPTION

Classification:
*Family.*—Rosaceae.
*Botanical.*—*Rubus* L. subgenus *Rubus*.
*Common name.*—Blackberry.
*Variety name.*—'DrisBlackFour'.

Parentage:

*Female parent.*—Proprietary blackberry plant named 'Sleeping Beauty' (U.S. Plant Pat. No. 13,758).

*Male parent.*—Proprietary blackberry plant named 'BH917-6' (unpatented).

Plant:

*Vigor* (*health and hardiness of plant*).—Low.

*Growth habit.*—Upright.

*Productivity.*—Medium.

*Propagation.*—Tissue culture and root cuttings.

*Self-fruitfulness.*—Self-fruitful.

*Time of bud burst.*—Late.

Canes:

*Fruiting lateral length* (*4th lateral from tip*).—Average: Medium; 39.5 cm. Range: 35.0 cm to 45.0 cm.

*Number of fruit per lateral.*—Average: 10.0. Range: 8.0 to 12.0.

*Fruiting on current year's cane.*—Present.

*Cane internodal distance.*—Average: 6.1 cm. Range: 5.0 cm to 7.0 cm.

*Number of new canes during flowering.*—Many.

*New cane strength* (*observed full-grown shoot after picking*).—Medium.

*Glaucosity observed on full-grown shoot after picking.*—Medium.

*Spines.*—Size: Large. Color: RHS 151A (Light yellow-green). Density on central third of cane: Medium. Texture: Rigid. Attitude of apex in relation to cane: Outwards.

*Young shoots.*—Quantity: Medium. Emergence from soil: Early. Anthocyanin coloration (during rapid growth): Medium; RHS 146A (Dark yellow-green). Intensity of green color: Medium; RHS 144A (Medium yellow-green). Number of glandular hairs: Absent or few.

*Dormant cane.*—Length: Long. Diameter (in central third): Medium. Cross section (from mid cane observed at end of first growing season): Rounded. Color: RHS 146A (Dark yellow-green). Number of branches: Many. Distribution of branches: Over whole length. Anthocyanin coloration: Weak; RHS 139C (Medium green). Spines: Present. Number of spines: Few.

Leaves:

*Type.*—Odd-pinnate.

*Predominant number of leaflets.*—3.

*Overlapping or relative position of lateral leaflets.*—Touching.

*Color.*—Upper surface: RHS 146A (Dark yellow-green). Lower surface: RHS 146B (Dark yellow-green).

*Arrangement.*—Opposite.

*Glossiness.*—Very weak.

*Cross section profile.*—Convex (margins rolled backwards).

*Leaflets.*—Shape: Ovate. Margin: Crenate. Depth of incisions: Shallow. Type of incision margin: Bi-serrate. Apex: Truncate. Base: Obtuse. Rachis length between terminal leaflet and adjacent lateral leaflet: Average: 1.2 cm. Range: 0.5 cm to 1.7 cm.

*Lateral leaflet* (*basal pair*).—Length: Average: 7.3 cm. Range: 6.2 cm to 8.8 cm. Width: Average: 4.7 cm. Range: 4.1 cm to 5.4 cm. Length/width ratio: 1.5.

*Terminal leaflet.*—Length: Average: Medium; 9.0 cm. Range: 6.4 cm to 11.0 cm. Width: Average: Medium; 7.0 cm. Range: 5.0 cm to 10.0 cm. Length/width ratio: 1.3. Lobing: Absent. Undulation of margin (rippling of margin): Medium. Blistering between veins (rugosity): Very weak. Shape: Oval to ovate. Tip: Complex. Base: Obtuse. Margin: Crenate. Cross-section: V-shaped.

*Petiole.*—Length average: 4.5 mm. Length range: 3.0 mm to 6.0 mm. Diameter average: 1.48 mm. Diameter range: 1.1 mm to 1.8 mm. Pigmentation: Upper surface: Lightly; RHS 146C (Medium yellow-green). Lower surface: Medium; RHS 152A (Medium yellow-green).

*Stipule.*—Size: Medium. Orientation: Erect.

Inflorescence:

*Time of beginning of flowering on previous year's cane.*—Late.

*Time of beginning of flowering on current year's cane.*—Late.

*Flower diameter.*—Average: Medium; 4.76 cm. Range: 4.20 cm to 5.40 cm.

*Flower number* (*at 3rd node from tip of lateral*).—Average: 4. Range: 4 to 5.

*Petal.*—Length: Average: 2.4 cm. Range: 2.1 cm to 2.7 cm. Width: Average: 1.6 cm. Range: 1.4 cm to 1.8 cm. Length/width ratio: 1.5. Color: RHS 155B (White).

*Pedicel.*—Length: Average: 21.55 mm. Range: 7.51 mm to 37.94 mm. Diameter: Average: 1.33 mm. Range: 1.04 mm to 1.83 mm.

Fruit:

*Time of ripening on previous year's cane.*—Medium.

*Time of ripening on current year's cane.*—Medium.

*Harvest interval.*—Mid January through mid March.

*Color.*—Immature: RHS 151A (Light yellow-green). Maturing: RHS 183A (Dark greyed-purple). Mature: RHS N186A (Dark greyed-purple).

*Glossiness.*—Medium.

*Shape in longitudinal section.*—Long conical.

*Size.*—Large.

*Length.*—Average: Medium; 3.25 cm. Range: 2.90 cm to 3.60 cm.

*Width.*—Average: Medium; 2.14 cm. Range: 1.70 cm to 2.50 cm.

*Ratio of length to width.*—1.5; Longer than broad.

*Weight* (*g/fruit*).—13.2.

*Soluble solids* (%) (*in Brix*).—16.0.

*Titratable acidity:* (% *as citric acid*).—0.89.

*Seed weight* (*g/seed*).—0.00463579.

*Number of druplets/fruit.*—100.

*Size of druplet.*—Medium.

*Firmness.*—Very firm.

*Yield.*—High.

Disease, pest, and stress resistance:

*Botrytis fruit rot.*—Resistant.

*Powdery mildew.*—Resistant.

*Verticillium wilt.*—Resistant.

*Leather rot.*—Resistant.

*Leaf scorch.*—Resistant.

*Leaf blight.*—Resistant.

*Black root rot.*—Resistant.

*Tetranychus urticae.*—Moderately resistant.

*Tarsonemus pallidus.*—Moderately resistant.

*Aphelenchoides fragariae.*—Moderately resistant.

*Pratylenchus penetrans.*—Moderately resistant.

*Ditylenchus dipsaci.*—Moderately resistant.

*Anthonomus rubi.*—Moderately resistant.

*Aphis spp.* (*Aphids*).—Moderately resistant.

*Lygus hesperus* (*Lygus bug*).—Moderately resistant.

COMPARISON WITH PARENTAL AND COMMERCIAL VARIETIES

'DrisBlackFour' differs from the female parent 'Sleeping Beauty' (U.S. Plant Pat. No. 13,758) in that 'DrisBlackFour' has medium productivity, very firm fruit, and long conical shaped fruit in longitudinal section, whereas 'Sleeping Beauty' has moderately high productivity, medium firm fruit, and elliptical shaped fruit in longitudinal section. Additionally, 'DrisBlackFour' has dormant canes that are rounded in cross-section, whereas 'Sleeping Beauty' has dormant canes that are angular to grooved in cross section.

'DrisBlackFour' differs from the proprietary male parent 'BH917-6' (unpatented) in that 'DrisBlackFour' has smaller fruit, better flavor, and less fruit breakdown in storage than 'BH917-6'. Additionally, 'DrisBlackFour' has plants that are darker green in color than 'BH917-6'.

'DrisBlackFour' differs from the commercial variety 'Driscoll Eureka' (U.S. Plant Pat. No. 14,765) in that 'DrisBlackFour' has an upright growth habit, late flowering, medium fruit glossiness, and large sized fruit, whereas 'Driscoll Eureka' has an semi-erect growth habit, very early flowering, strong fruit glossiness, and medium sized fruit.

We claim:

1. A new and distinct variety of blackberry plant named 'DrisBlackFour' as described and shown herein.

* * * * *